(12) United States Patent
De Paulis

(10) Patent No.: US 6,352,554 B2
(45) Date of Patent: *Mar. 5, 2002

(54) PROSTHETIC TUBULAR AORTIC CONDUIT AND METHOD FOR MANUFACTURING THE SAME

(75) Inventor: Ruggero De Paulis, Rome (IT)

(73) Assignee: Sulzer Vascutek Limited, Inchinnan (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/301,839

(22) Filed: Apr. 29, 1999

Related U.S. Application Data

(60) Provisional application No. 60/084,710, filed on May 8, 1998.

(51) Int. Cl.⁷ .............................. A61F 2/06; A61F 2/24
(52) U.S. Cl. .................... 623/1.26; 623/1.29; 623/1.28; 623/1.24
(58) Field of Search .............................. 623/1.15, 1.16, 623/1.24, 1.26, 1.3, 23.64, 23.68, 1.28, 1.29, 1.1, 1.6

(56) References Cited

U.S. PATENT DOCUMENTS

| 4,086,665 A | 5/1978 | Poirier ............................. 3/1.4 |
| 4,350,492 A | 9/1982 | Wright et al. ................. 8/94.11 |
| 5,123,919 A | 6/1992 | Sauter et al. .................... 623/2 |
| 5,139,515 A | 8/1992 | Robicsek ........................ 623/1 |
| 5,476,506 A | 12/1995 | Lunn ............................. 623/1 |
| 5,788,626 A | * 8/1998 | Thompson .................. 623/1.15 |

FOREIGN PATENT DOCUMENTS

| EP | 0 666 066 A1 | 8/1995 |
| EP | 0 666 066 B1 | 6/1999 |
| GB | 2 312 485 A | 10/1997 |

OTHER PUBLICATIONS

David et al., "An aortic valve–sparing operation for patients with aortic incompetence . . . ", from The Journal of Thoracic & Cardiovascular Surgery, vol. 103, No. 4, Apr. 1992, pp. 617–622.

Thubrikar et al., "Stress Sharing Between the Sinus and Leaflets of Canine Aortic Valve",, from The Annals of Thoracic Surgery, vol. 42, No. 4, Oct. 1986, pp. 434–440.

(List continued on next page.)

Primary Examiner—Bruce Snow
Assistant Examiner—Brian E. Pellegrino
(74) Attorney, Agent, or Firm—Ratner & Prestia

(57) ABSTRACT

A prosthetic aortic conduit for replacing a root portion of an aorta is provided. The conduit comprises a first tubular portion and a second tubular portion which are connected together along a substantially common axis. The second tubular portion does not substantially deform in a longitudinal direction and has resilient means which allow said second portion to be expandable in a lateral direction. This second portion is able to deform laterally to mimic the function of the sinuses of Valsalva. The method of manufacturing such a conduit comprises the steps of: a) providing a first tubular conduit suitable for use in heart surgery and having a longitudinal axis and first resilient means allowing some expansion in the longitudinal direction only;

b) securing to one of the ends of this first conduit a second tubular conduit suitable for use in heart surgery, this second conduit having second resilient means which allows some expansion in the lateral direction only.

12 Claims, 6 Drawing Sheets

OTHER PUBLICATIONS

Cabrol et al., "Complete replacement of the ascending aorta with reimplantation of the coronary arteries", J. Thorac. Cardiovasc. Surg., vol. 81, No. 2, Feb. 1981, pp. 309–315.

Bentall et al., "A technique for complete replacement of the ascending aorta", Thorax, 23, 338, 1968, pp. 338–339.

Kunzelman et al., "Aortic root and valve relationships", J. Thorac. Cardiovasc. Surg., vol. 107, No. 1, Jan. 1994, pp. 162–170.

Sarsam et al., "Remodeling of the aortic valve anulus", J. Thorac. Cardiovasc. Surg., vol. 105, No. 3, Mar. 1993, pp. 435–438.

Marian I. Ionescu, "Tissue Heart Valves", Figure 9.2, Right Ventricular Outflow Tract Reconstruction, The Butterworth Group, 1979.

* cited by examiner

PROSTHETIC TUBULAR AORTIC CONDUIT AND METHOD FOR MANUFACTURING THE SAME

This application claims benefit of provisional U.S. Ser. No. 60/084,710 filed May 8, 1998.

FIELD OF THE INVENTION

A prosthetic aortic conduit for replacing a root portion of the aorta and a method for manufacturing the same.

BACKGROUND OF THE INVENTION

The normal internal human aortic root conduit is provided with a sinus portion which has three sinuses (bulges) which surround the aortic valve. These sinuses are called sinuses of Valsalva and are arranged so that the cross-section of the sinus portion has a generally trefoil shape. The diameter and orifice area of the root are greater at the level of the sinus, decrease slightly at the base, but significantly decrease (by 20%) at the level of the sinotubular junction (where the sinus portion connects to the ascending portion of the aorta which supports the two iliac arteries).

The sinotubular junction or sinus ridge and the sinuses of Valsalva are known to be crucial for the normal function of the aortic valve. The sinus ridge is important in causing initial fluid flow eddies inside the sinuses of Valsalva (see Bellhouse B J: Velocity and pressure distributions in the aortic valve. *J Fluid Mech* 1969; 37(3): 587–600 and Bellhouse B. J.: The fluid mechanics of the aortic valve. In: Ionescu M. L. , Ross D. N., Woller G. H., eds. Biological tissue heart replacement. London: Butterworth-Heinemann, 1972:32–8). During systole, the aortic valve opens and the eddy currents created prevent the leaflets of the aortic valve from impacting on the aortic wall. Then, at the end of systole, the eddy currents inside the sinuses cause the leaflets of the aortic valve to become almost closed. Furthermore, the sinus curvature is very important in sharing stress with the leaflet. It has been demonstrated that during diastole the sinus walls move outwardly (increasing its circumferential curvature by 16%) taking up part of the load placed on the leaflet. Further it is known (see (Thubrikar M. J., Nolan S. P., Aouad J., Deck D.; Stress sharing between the sinus and leaflets of canine aortic valve. *Ann Thorac Surg* 1986; 42(4):434–40)) that the longitudinal length of the sinus changes very little or does not change at all during the cardiac cycle. In other words during the functioning of the aortic valve the sinus moves up and down as a whole without changing its length.

The standard surgical approach in patients with ascending aortic aneurysm or dissection involving the aortic root and associated with aortic valve disease is the replacement of the aortic valve and ascending aorta by means of a composite and valved graft onto which are reattached the two coronary arteries as originally described by Bentall and de Bono in their classical paper (Bentall H. H., De Bono A.: A technique for complete replacement of the ascending aorta, *Thorax* 1968; 23: 338–9). The "open" (Carrel button) method of coronary reimplantation was later recommended to decrease the tension on the coronary ostia while minimizing the risk of late false aneurysm formation. This "Carrel button" method has already reduced the incidence of pseudoaneurysm formation mainly through the reduction of the tension on the ostial anastomoses (see Svensson L. G.; Crawford E. S.; Hess K. R.; Coselli J. S.; Safi H. J.; Composite valve graft replacement of the proximal aorta: comparison of techniques in 348 patients. *Ann Thorac Surg* 1992, 54(3) 427–370). A modification of the standard technique was also introduced by Cabrol et al (Cabrol C, Pavie A, Gandjbakhch I. et al: Complete replacement of the ascending aorta with reimplantation of the coronary arteries. New Surgical approach, *J Thorac Cardiovasc Surg* 1981: 81; 309–15) for those cases of difficult presentation (low lying coronary ostia, calcified coronary ostia, tissue fibrosis in redo cases) where the coronary ostia are reattached to the aortic conduit by interposition of a small conduit made in DACRON. DACRON is the Trade Name for a material formed from straight chain polyester; the material may also be known as TERYLENE.

If the aortic valve leaflets are normal, a valve-sparing aortic root remodelling procedure which keeps the natural patient valve on site is a reasonable alternative in certain individuals. David and Feindel (David T. E., Feindel C. M.: An aortic valve-sparing operation for patients with aortic incompetence and aneurysm of the ascending aorta, *J Thorac Cardiovasc Surg* 1992; 103(4): 617–21) described a surgical technique where the dilated aortic root is replaced with a tube made of DACRON fibres and the native aortic valve is integrated within the graft. This method is generally known as the "Tirone David Type I aortic valve sparing procedure". However, the lack of sinuses in a straight tube graft was found to negatively influence proper valve function, with the consequent risk of decreasing valva longevity (Kunzelman K. S., Grande K. J., David T. E., Cochran R. P., Verrier E. D. : Aortic root and valve relationships. Impact on surgical repair *J Thorac Cardiovascular Surg* 1995; 109(2): 345–51).

Thus in the Tirone David Type I technique for valve sparing operations, the use of a straight tube without a sinus component raises several problems: opening and closing of the native valve is not optimal. For example, upon valve opening, the leaflets might impact on the graft and be potentially damaged. The absence or delay in eddy current formation might alter valve closure causing some regurgitation. Furthermore, the diastolic stress is borne only by the leaflet and is not shared with the sinuses causing a potential decrease in leaflet longevity.

An optimal design for root replacement should therefore incorporate sinuses and a sinotubular junction and further refinement of the technique consisted of trimming one end of the aortic tube graft to produce three separate extensions designed to replace the three sinuses. The reshaped DACRON tube was then sutured to the aortic valve remnants (see David T. E., Feindel C. M., Bos J.: Repair of the aortic valve in patients with aortic insufficiency and aortic root aneurysm. *J Thorac Cardiovasc Surg* 1995; 109(2):345–51) to obtain a final configuration resembling more closely the native aortic root. A similar technique was also described by Yacoub el al (Saram M. A., Yacoub M.: Remodeling of the aortic valve annulus. *J Thorac Cardiovasc Surg* 1993; 105(3): 435–8) several years previously.

In U.S. Pat. No. 5,139,515 it was proposed to provide an aortic graft having a lower portions provided with "bulges" apparently mimicking the sinuses of Valsalva. However no method to produce such a conduit for use in aortic surgery is described in the patent. U.S. Pat. No. 5,139,515 described a conduit having an "annular wall of a crimped material similar to that of conventional prosthesis". No indication is actually given of how to obtain the "annularly-spaced radially outward bulges" mimicking the sinuses. Moreover the drawings clearly show that the conduit, including the sinus portion, is provided along its whole length with corrugations which lie perpendicularly to the longitudinal axis of the prosethesis, and which impart longitudinal elasticity to the whole of the conduit. Upon implantation, the graft cannot expand radially outwardly, but has the potential to move and extend in the longitudinal direction of the longitudinal axis of the prosthesis.

Therefore there is still a need for an effective prosthetic conduit to replace the aortic root while providing all the advantages of the natural sinuses of Valsalva.

SUMMARY OF THE INVENTION

It is therefore one of the objects of the invention to provide a prosthetic aortic conduit which overcomes the drawbacks mentioned above and which upon implantation has the ability to expand radially outwardly whilst maintaining a degree of flexibility in the longitudinal direction.

It is another object of the invention to provide a conduit which is specifically designed to closely mimic the sinuses of Valsalva.

A first object of the invention is a prosthetic aortic conduit for replacing a root portion of an aorta which comprises a first tubular portion and a second tubular portion connected together along a substantially common axis. The second tubular portion does not substantially deform in a longitudinal direction and has resilient means which allow said second portion to be expandable in a lateral direction. As the second portion is able to deform laterally it is able to mimic the function of the sinuses of Valsalva.

It is preferred that the first tubular portion of the prosthetic aortic conduit of the invention be provided with resilient means which allow expansion of said first portion in a longitudinal direction.

It is also preferred that the prosthetic aortic conduit be made of polyester or PTFE material, including expanded PTFE material which may optionally be coated. A preferred material is DACRON.

It is further preferred that the second portion resilient means comprises longitudinally extending corrugations.

It is further preferred that the first portion resilient means of the conduit of the invention comprises annular corrugations successively provided along the longitudinal axis of said conduit.

It is further preferred that the first and second portions of the conduit be made of two distinct tubes which are secured together along said common axis.

It is further preferred that the conduit is provided with a third tubular portion which is connected to the second portion along the substantially common axis of the conduit. Advantageously this third tubular portion is provided with resilient means which allows expansion of said third portion in a longitudinal direction.

Optionally the conduit of the invention may be further provided with a prosthetic valve.

Another object of the invention is a method of manufacturing a prosthetic aortic conduit as described above. This method comprises the following steps:

a) providing a first tubular conduit suitable for use in heart surgery, the first conduit having a longitudinal axis and first resilient means allowing some expansion in the longitudinal direction only; and b) securing to one of the ends of this first conduit a second tubular conduit suitable for use in heart surgery so that the lumens of the first and second conduits are aligned and are continuous, the second conduit having a longitudinal axis and second resilient means which allows some expansion in the lateral direction only.

It is preferred that the first resilient means comprises a plurality of annular corrugations successively provided along the longitudinal axis of the first conduit and that the second resilient means comprises a plurality of longitudinally extending corrugations successively provided around the circumference of the second conduit.

It is also preferred that the second tubular conduit be made according to following steps:

a) taking a tubular conduit suitable for use in heart surgery, such conduit having annular corrugations allowing some expansion in the longitudinal direction only and having two opposite ends; and b) cutting said tubular conduit from end to end; and c) aligning and securing the two opposite ends together to obtain said second tubular conduit.

Where a third tubular conduit is required, this will simply be attached to the end of the second conduit which is not attached or not intended for attachment to the first conduit. Again the lumen of the third conduit should be commonly aligned with that of the second conduit. Optionally the third conduit may be attached to the combination of the first and second conduits. Alternatively the third conduit may be attached to the second conduit and then the first conduit attached. As described above, the third conduit will have circumferentially extending corrugations so will be similar to the first conduit in construction, but will generally be of a shorter length.

It is further preferred that the first, second and third tubular conduits are made of DACRON or PTFE material.

DESCRIPTION OF PREFERRED EMBODIMENTS OF THE INVENTION

Figure 1:
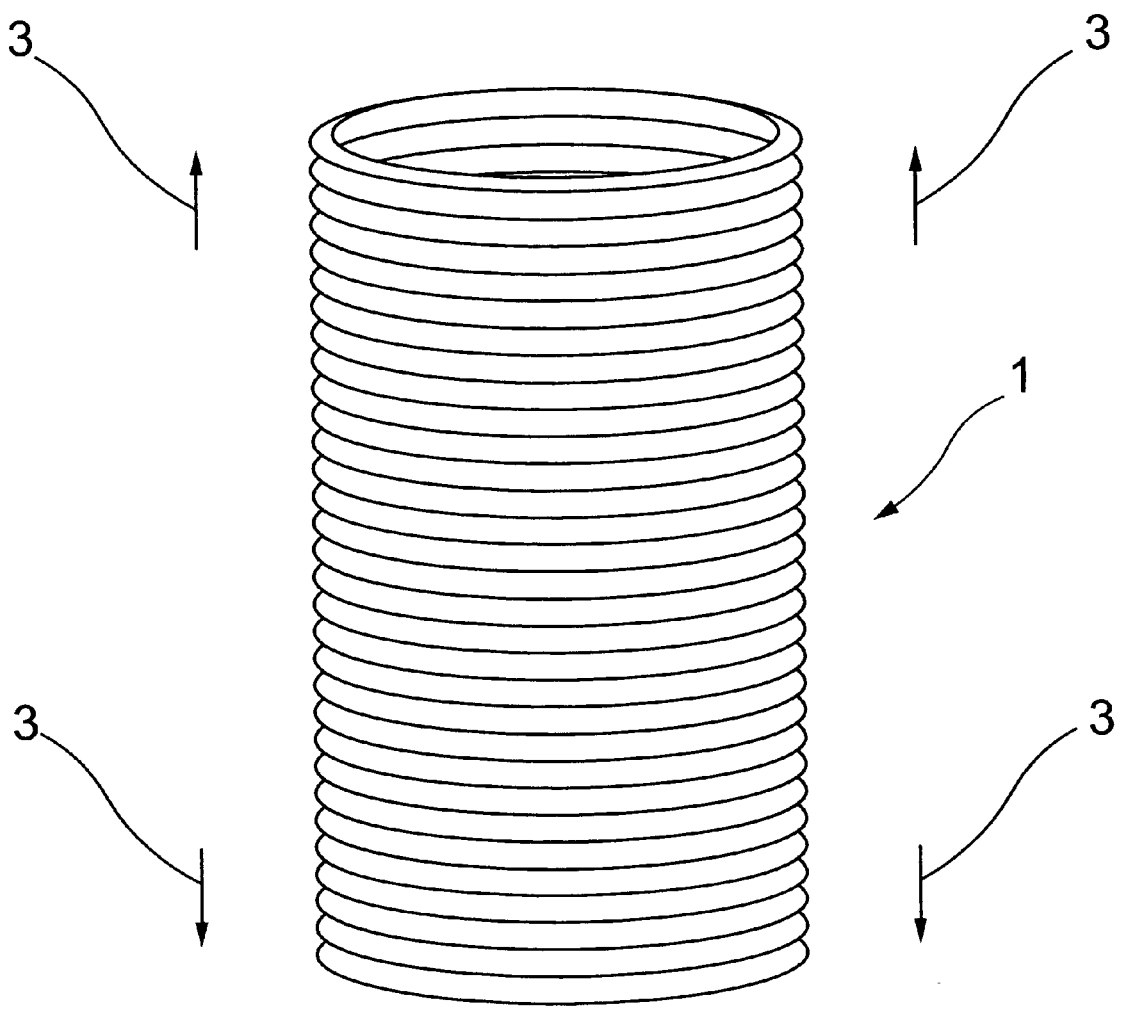
FIG. 1 is a representation of a known aortic conduit, showing corrugations which lie traverse to the longitudinal axis of the prosthesis.

FIG. 1 shows a standard aortic conduit 1 of the type currently used in aortic surgery. This conduit is made of DACRON but any suitable biocompatible material such as polytetrafluoroethylene (PTFE) could be used. This standard aortic conduit 1 includes circumferentially extending pleats so that the corrugations lie perpendicular to the longitudinal axis of the prosthesis. These corrugations provide a degree of expansion in the longitudinal direction (indicated by the black arrows 3 in FIG. 1) and the conduit 1 can therefore significantly increase its length.

Figure 2:
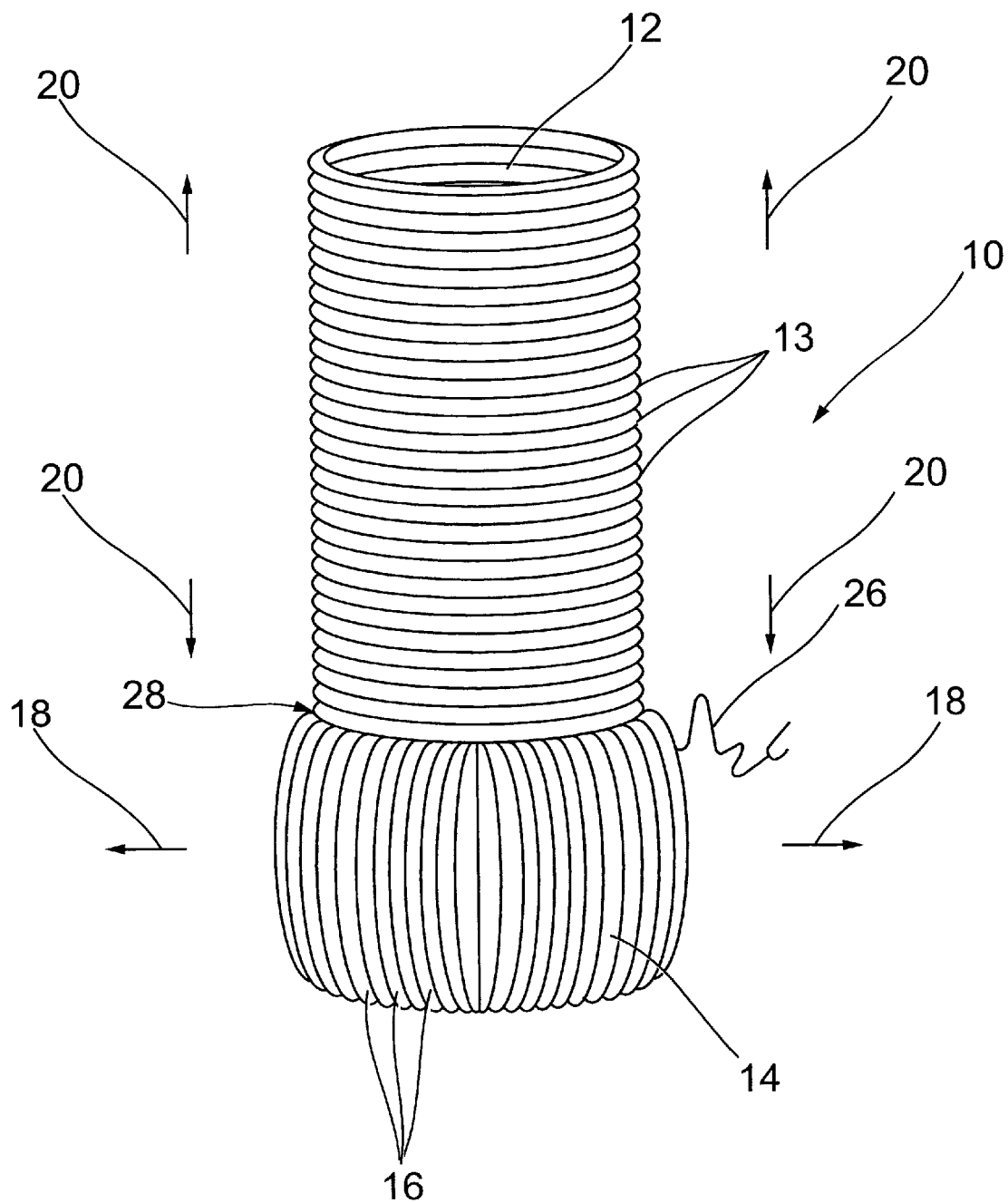
FIG. 2 is a prosthetic aortic conduit according to a first preferred embodiment of the invention.

FIG. 2 shows a preferred embodiment of the conduit of the invention. The conduit 10 comprises two distinct tubular portions having a common axis. The first upper portion 12 is made from a standard aortic conduit similar to the one shown in FIG. 1 and is provided with circumferentially extending corrugations 13 successively provided along the axis of the tubular first portion 12. The second lower portion, or skirt portion, 14 is a tube which can be made of the same material as the first portion (that is, any suitable biocompatible material, but preferably DACRON or PTFE) but which is provided with longitudinally extending pleats or corrugations 16. Each of these corrugations 16 extends in the general direction of the longitudinal axis of the prosthesis and is positioned substantially perpendicularly to the circumferential corrugations 13 of the first portion 12.

The proximal end of skirt portion 14 is attached to the distal end portion of the first portion 12 so the two connected portions have essentially the same lumen and form the tubular conduit 10.

The connection 28 between the first portion 12 and the skirt portion 14 (with their respective corrugations 13 and 16 orientated at an angle of about 90°) will act, upon implantation, as a "sinotubular junction" since its internal diameter will be significantly less than the internal diameter of its lower part, namely second portion 14. Once the prosthetic aortic conduit 10 is in place the internal diameter of the skirt portion 14 will vary during the cardiac cycle (systole/diastole) as in the natural aortic root. Thus, the skirt portion 14, when filled with blood under pressure, will stretch in the direction traverse to the longitudinal axis of the prosthesis (the lateral direction) mimicking the "sinuses of Valsalva". The pleat arrangement in skirt portion 14 does not however allow that section of the prosthesis to increase in length.

Thus the skirt portion 14 can move and expand in a lateral direction only, while the first portion 12 of the conduit 10 can extend in the longitudinal direction only. The resiliency of the skirt portion 14 in the general lateral direction is shown in FIG. 2 by the arrows 18 and the expansion of the first portion 12 in the general longitudinal direction is shown by the arrows 20.

Figure 2A:
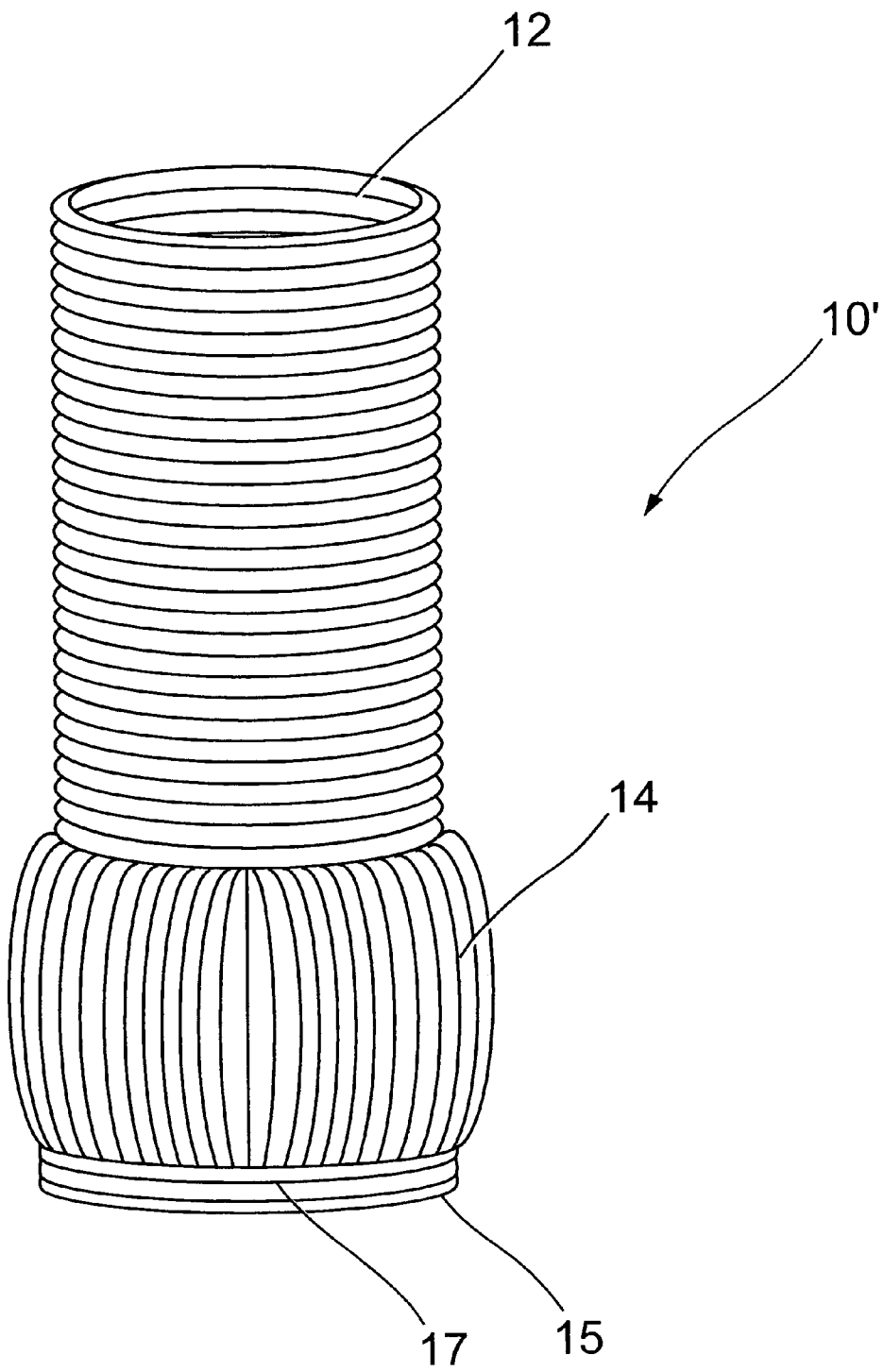
FIG. 2a is a prosthetic aortic conduit according to a second preferred embodiment of the invention.

In an alternative embodiment shown in FIG. 2a, a third tubular portion 15 is attached to the distal end of the skirt portion 14. The third tubular portion 15 is aligned on the same common axis as the first and second portions 12 and 14. The third portion 15 is aligned on the same common axis as the first and second portions 12 and 14. The third portion 15 is advantageously a short piece of standard aortic conduit, similar to that shown in FIG. 1. It is typically made of DACRON or similar material and is provided with circumferentially extending corrugations or pleats 17 in the same manner as the first portion 12.

Generally, the length of the third portion 15 will be short compared to the length of the first and second portions 12 and 14 and the presence of two or three corrugations 17 in the third portion 15 will normally be sufficient.

PREFERRED METHOD OF MANUFACTURE OF A CONDUIT ACCORDING TO THE INVENTION

The conduit 10 may be either manufactured independently or obtained according to the following method which is a further preferred embodiment of the invention and which is described with reference to FIGS. 3 and 4.

Figure 3:
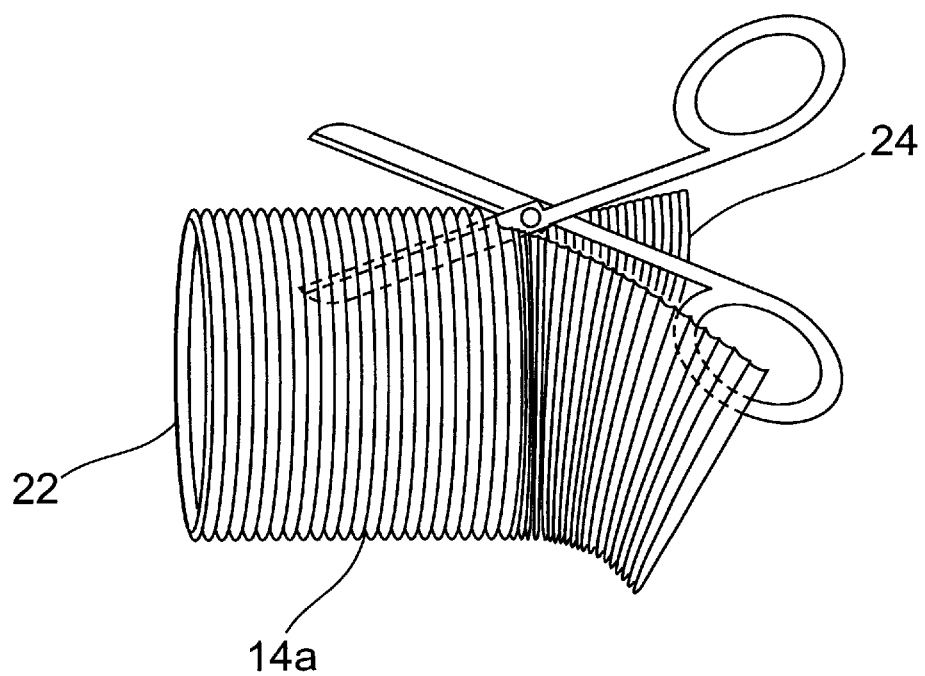
FIGS. 3 and 4 are schematic views of successive steps of manufacturing the aortic conduit shown in FIGS. 2 or 2a (included in a preferred method of the invention)

First, to obtain a skirt portion 14 like the one shown in FIGS. 2 or 2a a portion of a standard tube 14a (see FIG. 3) having annular corrugations provided along its axis is cut open from end to end as shown in FIG. 3. Preferably the material chosen will be DACRON. The tube 14a has a diameter approximately equal to the desired final length of skirt portion 14. Also, the length of tube 14a is chosen to correspond to the desired diameter of the skirt portion 14.

Figure 4:
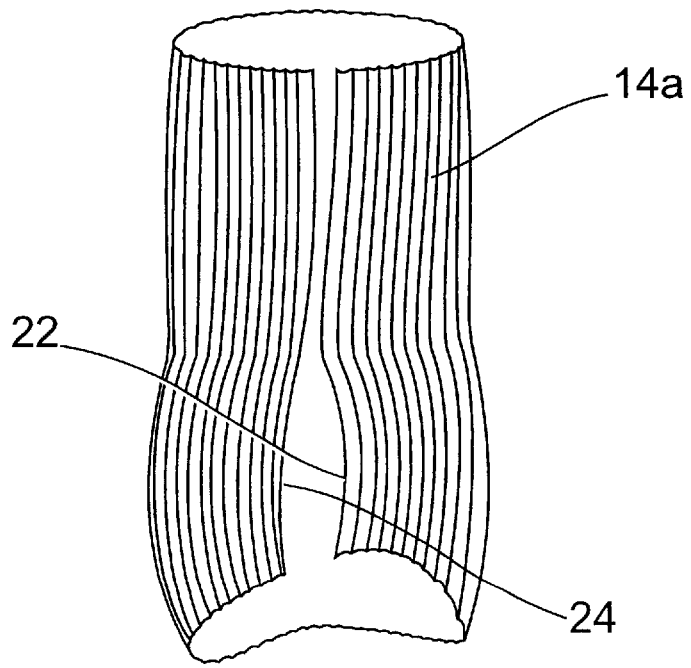

Once tube 14a has been cut open, the two end ridges 22 and 24 of the tube 14a are secured together (for example by suture) as shown in FIG. 4 and a skirt portion 14 is thus obtained.

A standard annularly corrugated tube, also preferably made of DACRON or similar material, is then provided to form the first portion 12 and the two portions 12 and 14 of the aortic conduit according to the invention are then secured together. As shown in FIG. 2 which relates to the first preferred embodiment of the invention, the two portions 12 and 14 may be sutured together using a thread 26.

It should be noted that while making the conduit 10 the length of the skirt portion 14 should be long enough to be trimmed according to the patient anatomy in aortic valve sparing operations.

The conduit 10' shown in FIG. 2a can be made by securing a third tubular portion 15 to the distal end of the skirt 14 of a conduit 10 shown in FIG. 2 and made as above. This third portion 15 is preferably made of a small tubular section of a standard tube having annular corrugations provided along its axis (as in FIG. 1). The proximal end of the small tubular section is then secured to the distal end of skirt portion 14 by known methods, for example by suture.

Aortic conduits of the invention may be used and adapted to various surgical techniques known to those skilled in the art, including those being described in detail below.

1. Composite Valve Graft Replacement (Bentall Operation)

The use of the aortic conduit of the invention does not require any changes in this known standard surgical technique.

Figure 5:
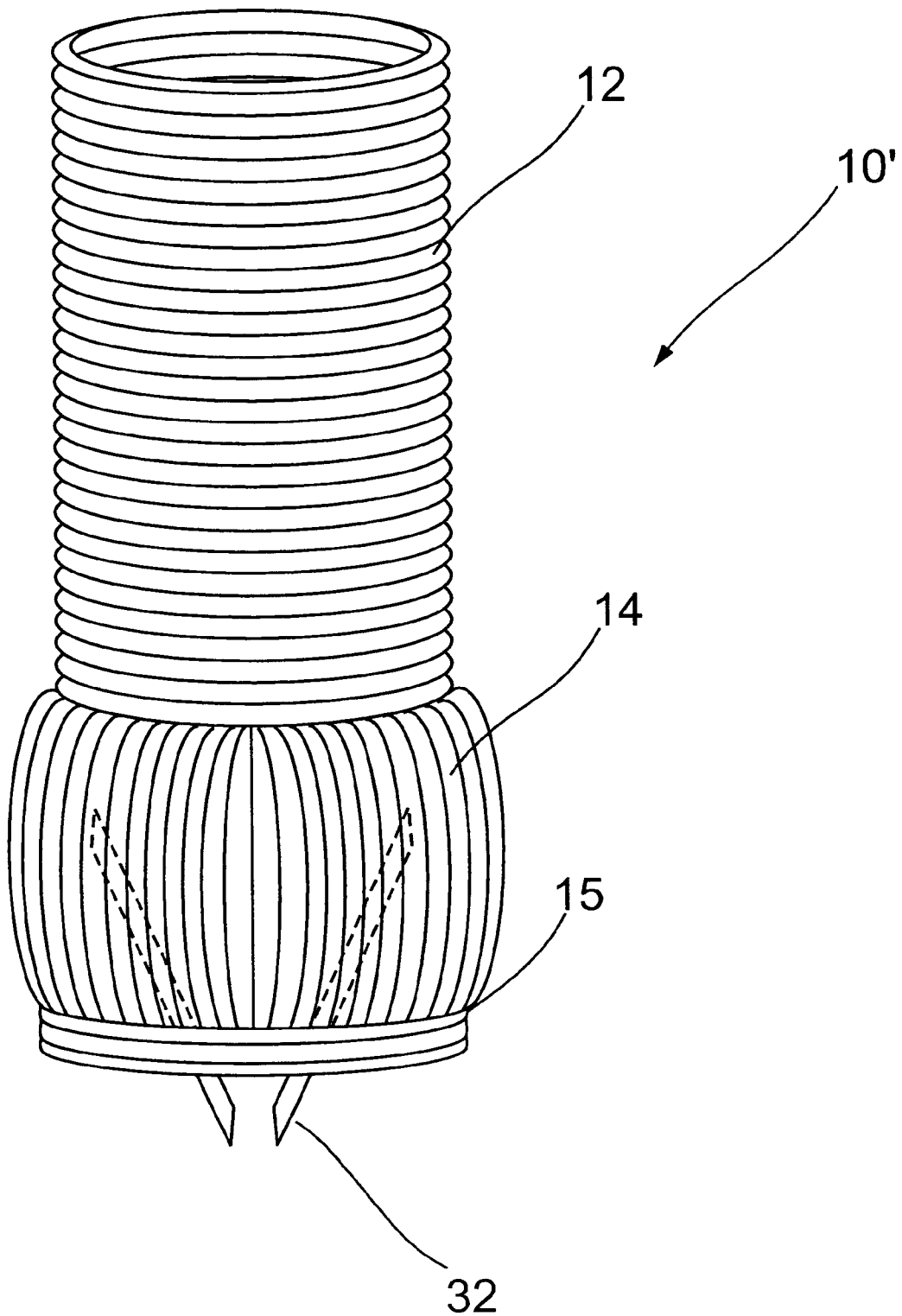
FIG. 5 is the embodiment of the aortic conduit shown in FIGS. 2 or 2a where the conduit has a prosthetic valve mounted thereon and is suitable for the Bentall type procedure.

FIG. 5 shows the conduit 10' of FIG. 2a adapted for the Bentall Operation. A standard bileaflet prosthetic valve 32 which is positioned partially inside the skirt portion 14. The prosthesis includes the annularly corrugated third portion 15 which is secured at the distal end of the skirt portion 14. This third portion 15 is attached to the heart and the skirt portion 14 mimics the sinuses of Valsalva. The coronary ostia are reattached to the conduit 10' either using the classical technique or the "open" technique (Carrel button) depending on the surgeon's preference. The presence of the third portion 15 facilitates attachment of the artificial valve of the prosthesis whilst the longitudinally corrugated skirt portion 14 gives several advantages over a standard DACRON graft tube.

The lateral resiliency of the skirt portion 14 reduces tension on the coronary ostia anastomoses not only during suturing but, most importantly, after the graft has been pressurised at the end of surgery. As a consequence, the modified aortic conduit 10' is particularly advantageous for use in cases where the coronary ostia are difficult to mobilise, difficult to reach (low lying coronary ostia) or where they are severely calcified.

Furthermore, at the end of the procedure, any undue tension along the long axis of the conduit 10' , instead of being directly transmitted to the coronary anastomoses, will be dampened by the sutures connecting the two portions of the conduit 10' as the skirt portion 14 of the conduit 10' (the new aortic root) is pulled as a whole.

2. Tirone David type I

Figure 6:
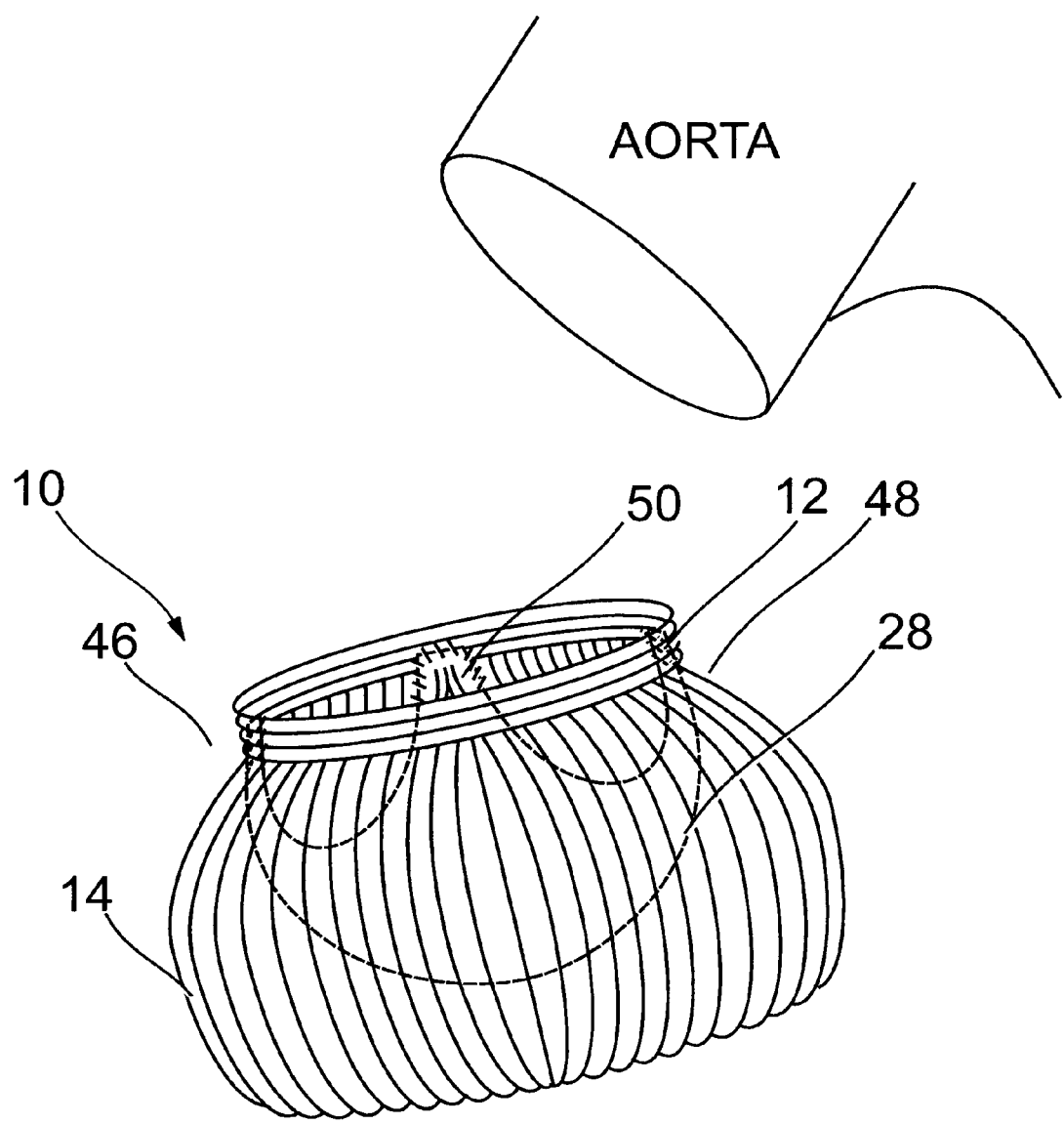
FIG. 6 schematically represents the prosthetic aortic conduit of FIG. 2 during use in a Tirone David Type I Aortic Valve Sparing Procedure.

A conduit according to the invention may also be used in classic "non-valved" aortic surgery known as "Tirone David type 1". The operation is carried out as originally described by David and Feindel in their previously mentioned paper and as known in the art. FIG. 6 illustrates the use of conduit 10 of FIG. 2 in the Tirone David type I procedure. Briefly, the three sinuses of Valsalva are excised leaving 5 mm of arterial wall attached to the patient's aortic valve and around the two coronary ostia, and multiple horizontal mattress sutures are passed below the aortic valve and then through the end of the aortic conduit 10. The conduit 10 is tailored so that the top of the three commissures 46, 48 and 50 will correspond to the "new sinotubular junction" (i.e. the junction 28 between the first portion 12 and the skirt portion 14) or a few mm above that junction 28. The first portion 12 of the conduit 10 is then cut 2 or 3 cm above the sutures. Next, the valve is secured to the graft in a manner similar to that for implanting a free-hand, subcoronary homograft aortic valve. Finally, the coronary ostia are reimplanted onto the conduit 10.

Once the conduit 10 is pressurised at the end of the surgical procedure, the lower part of the tube (skirt portion 14) will expand circumferentially creating new sinuses of Valsalva. The three commissures 46, 48 and 50, being fixed to junction 28 of the first portion 12 which do not expand circumferentially, will maintain their correct spacing and orientation (see FIG. 6). The presence of a new sinotubular junction and of artificial sinuses of Valsalva will ensure the creation of eddy currents with a more physiological opening and closure of the valve leaflets. Furthermore, the sinuses might have the potential of expanding circumferentially during the cardiac cycle with consequent reduced stress on the leaflet. The long term durability of the valve should therefore be greatly improved.

The conduit 10' of FIG. 2a could alternatively be used for this procedure.

Yacoub or Tirone David type II (or III)

Similarly, for the application of this surgical technique, the operation is carried out as previously described in using the aortic conduit according to the invention described with reference to FIG. 2. Briefly, the diseased aortic sinuses are excised down to the aortic annulus and an approximately sized conduit according to the invention is chosen. The skirt portion 14 of the conduit 10 is trimmed to produce three separate extensions, properly spaced, that will replace the sinuses. The height of the grooves is made so to reach the "new sinotubular junction " 28 of FIG. 2 or few mm above. Next, the top of the three commissures are fixed to the apex of each groove in a proper orientation. The excess of the conduit 10 is trimmed to precisely fit each sinus once it is sutured to the aortic annulus. Establishing the right length of the three extensions is facilitated because the skirt portion 14 does not stretch in the longitudinal direction. Finally, each extension is sutured to the remnants of arterial wall and aortic annulus surrounding the sinuses and then the coronary ostia are reimplanted onto the graft.

Compared to the standard DACRON graft tube, the use of the conduit of the invention offers the potential for a reduced tension on the coronary ostia anastomoses, an optimised circumferential expansion of the three sinuses with better stress sharing between the leaflet and the artificial sinus wall. The sinotubular junction is well defined and the maintenance of a good leaflets coaptation is assured by fixation of the top of each commissure to the portion of graft that does not expand circumferentially.

The prosthetic aortic conduit according to the invention is specifically designed to potentially fit all types of surgical operations above mentioned that are currently performed to treat pathologies of the aortic value and the aortic root.

I claim:

1. A prosthetic aortic conduit for replacing a root portion of an aorta, said conduit having first and second ends, wherein said conduit comprises a first tubular portion and a second tubular sinus portion connected together along a substantially common axis, wherein the first tubular portion forms the first end of the conduit, wherein said second sinus portion does not substantially deform in a longitudinal direction and has resilient means comprising longitudinally extending corrugations which allow said second sinus portion to be expandable in a later direction to mimic the function of the sinuses of Valsalva.

2. The prosthetic aortic conduit of claim 1, wherein said first portion is provided with resilient means which allow expansion of said first portion in a longitudinal direction.

3. The prosthetic aortic conduit of claim 1, wherein said conduit is made of DACRON or PTFE material.

4. The prosthetic aortic conduit of claim 3, wherein the first and second portions are made of two distinct tubes which are secured together along said common axis.

5. The prosthetic aortic conduit of claim 3, which is further provided with a prosthetic valve.

6. The prosthetic aortic conduit of claim 1, wherein said first portion resilient means comprises annular corrugations successively provided along the longitudinal axis of said first portion.

7. The prosthetic aortic conduit of claim 1, wherein a third tubular portion is connected to the second portion along said substantially common axis and wherein said third tubular portion is provided with resilient means which allow expansion of said third portion in a longitudinal direction.

8. A method of manufacturing a prosthetic aortic conduit having first and second ends, which comprises the following steps:
   a) providing a first tubular conduit suitable for use in heart surgery, said first conduit having a longitudinal axis and first resilient means allowing some expansion in the longitudinal direction only; and
   b) securing to one of the ends of this first conduit a second tubular sinus conduit suitable for use in heart surgery, said second sinus conduit having a circumference and second resilient means which allows some expansion in the lateral direction only; so that the first tubular portion forms the first end of the prosthetic aortic conduit.

9. The method of claim 8, wherein the first resilient means comprises a plurality of annular corrugations successively provided along the longitudinal axis of the first conduit and wherein the second resilient means comprises a plurality of longitudinally extending corrugations successively provided around the circumference of the second conduit.

10. The method of claim 9, wherein said second tubular conduit is made according to following steps:
   a) taking a tubular conduit suitable for use in heart surgery, said conduit having annular corrugations allowing some expansion in the longitudinal direction only and having two opposite ends; and
   b) cutting said tubular conduit from end to end; and
   c) aligning and securing the two opposite ends together to obtain said second tubular conduit.

11. The method of claim 9, wherein the first and second tubular conduits are made of Dacron or PTFE material.

12. A method of replacing a root portion of an aorta which comprises the sinuses of Valsalva, said method comprising the steps of:
   excising said portion of the aorta; and
   replacing said excised portion by providing a prosthetic conduit which comprises a first tubular portion and a second tubular sinus portion connected together along a substantially common axis, wherein said second portion does not substantially deform in a longitudinal direction and has resilient means comprising longitudinally extending corrugations which allow said second sinus portion to be expandable in a lateral direction to mimic the function of the sinuses of Valsalva.

* * * * *

UNITED STATES PATENT AND TRADEMARK OFFICE
CERTIFICATE OF CORRECTION

PATENT NO. : 6,352,554 B2
DATED : March 5, 2002
INVENTOR(S) : De Paulis

It is certified that error appears in the above-identified patent and that said Letters Patent is hereby corrected as shown below:

Column 8,
Line 2, should read:

-- tion to be expandable in a lateral direction to mimic the --

Signed and Sealed this

Twenty-fourth Day of September, 2002

Attest:

Attesting Officer

JAMES E. ROGAN
Director of the United States Patent and Trademark Office